(12) United States Patent
Venkatachalam et al.

(10) Patent No.: US 11,701,365 B2
(45) Date of Patent: Jul. 18, 2023

(54) FORMULATIONS COMPRISING CHLORPROMAZINE HYDROCHLORIDE, AND PROCESS OF PREPARATION THEREOF

(71) Applicant: ATOZ PHARMACEUTICALS PVT LTD, Chennai (IN)

(72) Inventors: Natarajan Venkatachalam, Chennai (IN); Olaganathan Arumugam, Chennai (IN)

(73) Assignee: ATOZ PHARMACEUTICALS PVT LTD, Chennai (IN)

( * ) Notice: Subject to any disclaimer, the term of this patent is extended or adjusted under 35 U.S.C. 154(b) by 291 days.

(21) Appl. No.: 16/858,021

(22) Filed: Apr. 24, 2020

(65) Prior Publication Data
US 2020/0352955 A1 Nov. 12, 2020

(30) Foreign Application Priority Data
May 9, 2019 (IN) .............................. 201941018595

(51) Int. Cl.
| | |
|---|---|
| *A61K 31/5415* | (2006.01) |
| *A61K 47/38* | (2006.01) |
| *A61K 9/28* | (2006.01) |
| *A61K 47/14* | (2017.01) |
| *A61K 47/26* | (2006.01) |
| *A61K 47/02* | (2006.01) |

(52) U.S. Cl.
CPC .......... *A61K 31/5415* (2013.01); *A61K 9/284* (2013.01); *A61K 47/02* (2013.01); *A61K 47/14* (2013.01); *A61K 47/26* (2013.01); *A61K 47/38* (2013.01)

(58) Field of Classification Search
CPC .... A61K 31/5415; A61K 9/284; A61K 47/02; A61K 47/14; A61K 47/26; A61K 47/38
See application file for complete search history.

(56) References Cited

U.S. PATENT DOCUMENTS 6,090,819 A * 7/2000 Rupniak ................ A61K 45/06 514/278

OTHER PUBLICATIONS

Remington Pharmaceutical Science, 18th Ed, 1995, p. 1413 (Year: 1995).*
Yousif et al., Annals of Agricultural Science, 2012;57(1):19-27 (Year: 2012).*
Handbook of Pharmaceutical Excipients, 6th Ed, 2009, pp. 185-188, 404-407, and 691-694. (Year: 2009).*

* cited by examiner

*Primary Examiner* — San Ming R Hui

(57) ABSTRACT

The present disclosure relates to a process for preparing a pharmaceutical formulation, said process comprises: i) blending chlorpromazine hydrochloride and microcrystalline cellulose under a first set of pre-determined conditions to obtain a first mixture; ii) blending lactose monohydrate with first mixture under a second set of pre-determined conditions to obtain a second mixture; iii) blending pregelatinized starch, colloidal silicon dioxide and magnesium stearate with second mixture under a third set of pre-determined conditions to obtain a third mixture; iv) screening the third mixture through #40 Mesh and dry blending under a fourth set of pre-determined conditions to obtain a fourth mixture; and v) directly compressing the fourth mixture to obtain the pharmaceutical formulation.

2 Claims, No Drawings

FORMULATIONS COMPRISING CHLORPROMAZINE HYDROCHLORIDE, AND PROCESS OF PREPARATION THEREOF

FIELD OF THE INVENTION

The present invention relates to the field of pharmaceutical formulations, and in particular relates to tablet dosage forms of chlorpromazine hydrochloride. The present disclosure also provides for a convenient process of preparation of the tablet dosage forms of chlorpromazine hydrochloride. The present is based on, and claims priority from an Indian Application Number 201941018595 filed on 9 May 2019, the disclosure of which is hereby incorporated by reference herein

BACKGROUND

Chlorpromazine, marketed under the trade names Thorazine and Largactil among others, belongs to the class of medications known as phenothiazines. It is used to treat mania and disorders with psychosis, such as schizophrenia. It is also used to prevent and treat nausea and vomiting. Chlorpromazine works by affecting the balance of chemicals in the brain.

Existing technologies to prepare chlorpromazine hydrochloride tablet dosage forms are largely based on utilizing wet granulation technique. Typically, wet granulation involved additional process steps such as wet milling, drying and milling of dried granulation which incurs energy, time and cost. Also, tablets prepared by wet methods often show incremental hardness as a function of time and storage temperature; and hence are more likely to show variable product performance. For example, WO2004082615 discloses a process for preparing sustained release tablets of chlorpromazine by wet granulation technique.

To overcome the drawbacks associated with wet granulation technique, research has been performed on the preparation of chlorpromazine hydrochloride tablets using a dry granulation process. For example, US20030021841A1 discloses a process for preparing a pharmaceutical tablet formulation of a poorly-compressible pharmaceutical agent, which comprises the steps of: (a) preparing a blend by combining the poorly-compressible pharmaceutical agent, a hydrophilic erodible component and a hydrophobic component; and (b) compressing the blend into a tablet. The requirement of at least one hydrophobic component and at least 1% by weight of formulation is critical as per the invention disclosure of US 2003/0021841 for poorly compressible drugs (like chlorpromazine Also, the invention requires multiple unit process or processor (i.e. either in fluid bed processor (FBP) or melting granulation (MG). It also requires higher energy input in form of heat to melt (in MG) or to coat (in FBP) the hydrophobic component.

The above information is presented as background information only to help the reader to understand the present invention. Applicants have made no determination and make no assertion as to whether any of the above might be applicable as prior art with regard to the present application.

OBJECT OF THE INVENTION

The principal object of the embodiments herein is to provide for a cost-effective process for preparation of tablet forms of chlorpromazine hydrochloride.

Another object of the invention is to provide for a simple process (direct compression) for preparation of tablet forms of chlorpromazine hydrochloride.

Yet another object of the embodiments herein is to provide for an energy-effective process for preparation of tablet forms of chlorpromazine hydrochloride.

SUMMARY OF THE INVENTION

Accordingly, the invention provides a pharmaceutical formulation comprising: a) chlorpromazine hydrochloride having a weight percentage in a range of 4-40% with respect to the pharmaceutical composition; b) magnesium stearate having a weight percentage in a range of 1-5% with respect to the pharmaceutical composition; c) lactose monohydrate having a weight percentage in a range of 30-55% with respect to the pharmaceutical composition; d) microcrystalline cellulose having a weight percentage in a range of 0-35% with respect to the pharmaceutical composition; e) pre-gelatinized starch having a weight percentage in a range of 3-15% with respect to the pharmaceutical composition; and f) colloidal silicon dioxide having a weight percentage in a range of 0.5-2.5%, with respect to the total mixture/ingredients in the pharmaceutical formulation.

In another aspect of the present disclosure, there is provided a process for preparation of the pharmaceutical formulation comprising: a) chlorpromazine hydrochloride having a weight percentage in a range of 4-40% with respect to the pharmaceutical composition; b) magnesium stearate having a weight percentage in a range of 1-5% with respect to the pharmaceutical composition; c) lactose monohydrate having a weight percentage in a range of 30-55% with respect to the pharmaceutical composition; d) microcrystalline cellulose having a weight percentage in a range of 0-35% with respect to the pharmaceutical composition; e) pre-gelatinized starch having a weight percentage in a range of 3-15% with respect to the pharmaceutical composition; and f) colloidal silicon dioxide having a weight percentage in a range of 0.5-2.5%, with respect to the total mixture/ingredients in the pharmaceutical formulation, said process comprising: i) blending chlorpromazine hydrochloride and microcrystalline cellulose under a first set of pre-determined conditions to obtain a first mixture; ii) blending lactose monohydrate with first mixture under a second set of pre-determined conditions to obtain a second mixture; iii) blending pre-gelatinized starch, colloidal silicon dioxide and magnesium stearate with second mixture under a third set of pre-determined conditions to obtain a third mixture; iv) screening the third mixture through #40 Mesh and dry blending again under a fourth set of pre-determined conditions to obtain a fourth mixture; and v) compressing the fourth mixture to obtain the pharmaceutical formulation.

These and other aspects of the embodiments herein will be better appreciated and understood when considered in conjunction with the following description. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

DETAILED DESCRIPTION OF INVENTION

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. Also, the various embodiments described herein are not necessarily mutually exclusive, as some embodiments can be combined with one or more other embodiments to form new embodiments. The term "or" as used herein, refers to a non-exclusive or, unless otherwise indicated. The examples used herein are intended merely to facilitate an understanding of ways in which the embodiments herein can be practiced and to further enable those skilled in the art to practice the embodiments herein. Accordingly, the examples should not be construed as limiting the scope of the embodiments herein.

Conventionally used compositions of chlorpromazine hydrochloride tablets are prepared by wet granulation processes which incur several process steps and impose huge costs on the time and energy. Although, dry granulation processes circumvent the problems associated with the use of wet granulation technique, methods used to prepare chlorpromazine using dry granulation require the use of hydrophobic components, and also incurs several process steps to process those components without any wetting agent or granulating fluid (Fluid bed processor or melting granulation). Therefore, the object of the present disclosure is to provide a cost-effective, energy-effective, simple (direct compression) process for preparation of homogenous tablet (optionally coated) form of chlorpromazine hydrochloride.

In an embodiment of the present disclosure, there is provided a pharmaceutical formulation comprising: a) chlorpromazine hydrochloride having a weight percentage in a range of 4-40% with respect to the pharmaceutical composition; b) magnesium stearate having a weight percentage in a range of 1-5% with respect to the pharmaceutical composition; c) lactose monohydrate having a weight percentage in a range of 30-55% with respect to the pharmaceutical composition; d) microcrystalline cellulose having a weight percentage in a range of 0-35% with respect to the pharmaceutical composition; e) pre-gelatinized starch having a weight percentage in a range of 3-15% with respect to the pharmaceutical composition; and f) colloidal silicon dioxide having a weight percentage in a range of 0.5-2.5%, with respect to the total mixture/ingredients in the pharmaceutical formulation. In another embodiment of the present disclosure, the pharmaceutical formulation comprising: a) chlorpromazine hydrochloride having a weight percentage of 33.33% with respect to the pharmaceutical composition; b) magnesium stearate having a weight percentage of 1.5% with respect to the pharmaceutical composition; c) lactose monohydrate having a weight percentage of 34.67% with respect to the pharmaceutical composition; d) microcrystalline cellulose having a weight percentage of 20% with respect to the pharmaceutical composition; e) pre-gelatinized starch having a weight percentage of 10% with respect to the pharmaceutical composition; and f) colloidal silicon dioxide having a weight percentage of 0.5%, with respect to the total mixture/ingredients in the pharmaceutical formulation.

In an embodiment of the present disclosure, there is provided a pharmaceutical formulation as described herein, wherein the pharmaceutical formulation contains about 10 mg to 200 mg of chlorpromazine hydrochloride. In another embodiment of the present disclosure, the pharmaceutical formulation contains 25 mg, 50 mg, 100 mg, and 200 mg of chlorpromazine hydrochloride.

In an embodiment of the present disclosure, there is provided a pharmaceutical formulation comprising: a) chlorpromazine hydrochloride having a weight percentage in a range of 4-40% with respect to the pharmaceutical composition; b) magnesium stearate having a weight percentage in a range of 1-5% with respect to the pharmaceutical composition; c) lactose monohydrate having a weight percentage in a range of 30-55% with respect to the pharmaceutical composition; d) microcrystalline cellulose having a weight percentage in a range of 0-35% with respect to the pharmaceutical composition; e) pre-gelatinized starch having a weight percentage in a range of 3-15% with respect to the pharmaceutical composition; and f) colloidal silicon dioxide having a weight percentage in a range of 0.5-2.5%, with respect to the total mixture/ingredients in the pharmaceutical formulation, and wherein the pharmaceutical formulation contains about 10 mg to 200 mg of chlorpromazine hydrochloride.

In an embodiment of the present disclosure, there is provided a process for preparation of a pharmaceutical formulation comprising: a) chlorpromazine hydrochloride having a weight percentage in a range of 4-40% with respect to the pharmaceutical composition; b) magnesium stearate having a weight percentage in a range of 1-5% with respect to the pharmaceutical composition; c) lactose monohydrate having a weight percentage in a range of 30-55% with respect to the pharmaceutical composition; d) microcrystalline cellulose having a weight percentage in a range of 0-35% with respect to the pharmaceutical composition; e) pre-gelatinized starch having a weight percentage in a range of 3-15% with respect to the pharmaceutical composition; and f) colloidal silicon dioxide having a weight percentage in a range of 0.5-2.5%, with respect to the total mixture/ingredients in the pharmaceutical formulation, said process comprising: i) blending chlorpromazine hydrochloride and microcrystalline cellulose under a first set of pre-determined conditions to obtain a first mixture; ii) blending lactose monohydrate with first mixture under a second set of pre-determined conditions to obtain a second mixture; iii) blending pre-gelatinized starch, colloidal silicon dioxide and magnesium stearate with second mixture under a third set of pre-determined conditions to obtain a third mixture; iv) Screening the third mixture through #40 Mesh and blend again under a fourth set of pre-determined conditions to obtain a fourth mixture; and v) compressing the fourth mixture to obtain the pharmaceutical formulation. In an embodiment, the process is a dry blending (direct compression) process. Dry blending (direct compression) refers to a process that is performed without the use of any wetting agent or granulating fluid.

In an embodiment of the present disclosure, there is provided a process for preparation of a pharmaceutical formulation comprising: a) chlorpromazine hydrochloride having a weight percentage in a range of 4-40% with respect to the pharmaceutical composition; b) magnesium stearate having a weight percentage in a range of 1-5% with respect to the pharmaceutical composition; c) lactose monohydrate having a weight percentage in a range of 30-55% with respect to the pharmaceutical composition; d) microcrystalline cellulose having a weight percentage in a range of 0-35% with respect to the pharmaceutical composition; e) pre-gelatinized starch having a weight percentage in a range of 3-15% with respect to the pharmaceutical composition; and f) colloidal silicon dioxide having a weight percentage in a range of 0.5-2.5%, with respect to the total mixture/ingredients in the pharmaceutical formulation, said process comprising: i) blending chlorpromazine hydrochloride and microcrystalline cellulose under a first set of pre-determined conditions to obtain a first mixture, wherein the first set of pre-determined conditions include a period of 3-6 minutes at 10-20 rpm; ii) blending lactose monohydrate under a second set of pre-determined conditions to obtain a second mixture, wherein the second set of pre-determined conditions include a period of 8-12 minutes at 10-20 rpm; iii) blending pre-gelatinized starch, colloidal silicon dioxide and magnesium stearate for under a third set of pre-determined conditions to obtain a third mixture, wherein the third set of pre-determined conditions include a period of 3-6 minutes at 10-20 rpm; iv) screening the third mixture through #40 mesh; v) dry blending the third mixture after sieving, under a fourth set of pre-determined conditions that include a period of 3-6 minutes at 10-20 rpm; and vi) directly compressing the fourth mixture to obtain the pharmaceutical formulation. In an embodiment, the process is a dry blending (direct compression) process.

In an embodiment of the present disclosure, there is provided a process for preparation of a pharmaceutical formulation comprising: a) chlorpromazine hydrochloride having a weight percentage in a range of 4-40% with respect to the pharmaceutical composition; b) magnesium stearate having a weight percentage in a range of 1-5% with respect to the pharmaceutical composition; c) lactose monohydrate having a weight percentage in a range of 30-55% with respect to the pharmaceutical composition; d) microcrystalline cellulose having a weight percentage in a range of 0-35% with respect to the pharmaceutical composition; e) pre-gelatinized starch having a weight percentage in a range of 3-15% with respect to the pharmaceutical composition; and f) colloidal silicon dioxide having a weight percentage in a range of 0.5-2.5%, with respect to the total mixture/ingredients in the pharmaceutical formulation, said process comprising: i) blending chlorpromazine hydrochloride and microcrystalline cellulose under a first set of pre-determined conditions to obtain a first mixture, wherein the first set of pre-determined conditions include a period of 3-6 minutes at 10-20 rpm; ii) blending lactose monohydrate with first mixture under a second set of pre-determined conditions to obtain a second mixture, wherein the second set of pre-determined conditions include a period of 8-12 minutes at 10-20 rpm; iii) blending pre-gelatinized starch, colloidal silicon dioxide and magnesium stearate with second mixture under a third set of pre-determined conditions to obtain a third mixture, wherein the third set of pre-determined conditions include a period of 3-6 minutes at 10-20 rpm; iv) screening the third mixture through a #40 mesh screen; v) dry blending the third mixture after sieving, under a fourth set of pre-determined conditions to obtain a fourth mixture, and wherein the fourth set of pre-determined conditions include a period of 3-6 minutes at 10-20 rpm; and vi) directly compressing the fourth mixture to obtain the pharmaceutical formulation. In an embodiment, the process is dry blending (direct compression) process. In another embodiment, the first set of pre-determined conditions include a period of 5 minutes at 15 rpm; ii) blending lactose monohydrate under a second set of pre-determined conditions to obtain a second mixture, wherein the second set of pre-determined conditions include a period of 10 minutes at 15 rpm; iii) blending pre-gelatinized starch, colloidal silicon dioxide and magnesium stearate for under a third set of pre-determined conditions to obtain a third mixture, wherein the third set of pre-determined conditions include a period of 5 minutes at 15 rpm; iv) sieving the third mixture through a #40 mesh screen v) dry blending the third mixture after sieving under a fourth set of pre-determined conditions to obtain a fourth mixture, and wherein the fourth set of pre-determined conditions include a period of 5 minutes at 15 rpm; and vi) directly compressing the fourth mixture to obtain the pharmaceutical formulation. In an embodiment, the process is a dry blending (direct compression) process.

In an embodiment of the present disclosure, there is provided a process for preparation of the pharmaceutical formulation as described herein, wherein the process is dry blending (direct compression) process suggesting that the process is performed without any wetting agent or granulating fluid.

In an embodiment of the present disclosure, there is provided a process for preparation of a pharmaceutical formulation comprising: a) chlorpromazine hydrochloride having a weight percentage in a range of 4-40% with respect to the pharmaceutical composition; b) magnesium stearate having a weight percentage in a range of 1-5% with respect to the pharmaceutical composition; c) lactose monohydrate having a weight percentage in a range of 30-55% with respect to the pharmaceutical composition; d) microcrystalline cellulose having a weight percentage in a range of 0-35% with respect to the pharmaceutical composition; e) pre-gelatinized starch having a weight percentage in a range of 3-15% with respect to the pharmaceutical composition; and f) colloidal silicon dioxide having a weight percentage in a range of 0.5-2.5% with respect to the pharmaceutical composition, with respect to the total mixture/ingredients in the pharmaceutical formulation, said process comprising: i) blending chlorpromazine hydrochloride and microcrystalline cellulose under a first set of pre-determined conditions to obtain a first mixture; ii) blending lactose monohydrate with first mixture under a second set of pre-determined conditions to obtain a second mixture; iii) blending pre-gelatinized starch, colloidal silicon dioxide and magnesium stearate with second mixture under a third set of pre-determined conditions to obtain a third mixture; iv) screening the third mixture through #40 Mesh and dry blending again under a fourth set of pre-determined conditions to obtain a fourth mixture; and v) directly compressing the fourth mixture to obtain the pharmaceutical formulation. In an embodiment, the process is a dry blending (direct compression) process.

In an embodiment of the present disclosure, there is provided a process for preparation of the pharmaceutical formulation as described herein, wherein the pharmaceutical formulation is optionally coated with a film. In an embodiment, the film coating is done with a PVA (polyvinyl alcohol) based coating system. In another embodiment, the PVA based coating system is composed of PVA, polyethylene glycol (Macrogol), talc, titanium dioxide and colorants.

In an embodiment of the present disclosure, there is provided a process for preparation of a pharmaceutical formulation comprising: a) chlorpromazine hydrochloride having a weight percentage in a range of 4-40% with respect to the pharmaceutical composition; b) magnesium stearate having a weight percentage in a range of 1-5% with respect to the pharmaceutical composition; c) lactose monohydrate having a weight percentage in a range of 30-55% with respect to the pharmaceutical composition; d) microcrystalline cellulose having a weight percentage in a range of 0-35% with respect to the pharmaceutical composition; e) pre-gelatinized starch having a weight percentage in a range of 3-15% with respect to the pharmaceutical composition; and f) colloidal silicon dioxide having a weight percentage in a range of 0.5-2.5% with respect to the pharmaceutical composition, with respect to the total mixture/ingredients in the pharmaceutical formulation, said process comprising: i)

blending chlorpromazine hydrochloride and microcrystalline cellulose under a first set of pre-determined conditions to obtain a first mixture; ii) blending lactose monohydrate with first mixture under a second set of pre-determined conditions to obtain a second mixture; iii) blending pre-gelatinized starch, colloidal silicon dioxide and magnesium stearate with second mixture under a third set of pre-determined conditions to obtain a third mixture; iv) screening the third mixture through a #40 mesh screen v) dry blending the third mixture after sieving under a fourth set of pre-determined conditions to obtain a fourth mixture; vi) directly compressing the fourth mixture to obtain the pharmaceutical formulation; and vii) optionally film coating the pharmaceutical formulation with PVA based coating system.

In an embodiment of the present disclosure, there is provided a process for preparation of a pharmaceutical formulation comprising: a) chlorpromazine hydrochloride having a weight percentage in a range of 4-40% with respect to the pharmaceutical composition; b) magnesium stearate having a weight percentage in a range of 1-5% with respect to the pharmaceutical composition; c) lactose monohydrate having a weight percentage in a range of 30-55% with respect to the pharmaceutical composition; d) microcrystalline cellulose having a weight percentage in a range of 0-35%; e) pre-gelatinized starch having a weight percentage in a range of 3-15% with respect to the pharmaceutical composition; and f) colloidal silicon dioxide having a weight percentage in a range of 0.5-2.5% with respect to the pharmaceutical composition, with respect to the total mixture/ingredients in the pharmaceutical formulation, said process comprising: i) blending chlorpromazine hydrochloride and microcrystalline cellulose under a first set of pre-determined conditions to obtain a first mixture, wherein the first set of pre-determined conditions include a period of 3-6 minutes at 10-20 rpm; ii) blending lactose monohydrate under a second set of pre-determined conditions to obtain a second mixture, wherein the second set of pre-determined conditions include a period of 8-12 minutes at 10-20 rpm; iii) blending pre-gelatinized starch, colloidal silicon dioxide and magnesium stearate for under a third set of pre-determined conditions to obtain a third mixture, wherein the third set of pre-determined conditions include a period of 3-6 minutes at 10-20 rpm; iv) Screen the third mixture through #40 Mesh and dry blending under a fourth set of pre-determined conditions to obtain a fourth mixture, and wherein the fourth set of pre-determined conditions include a period of 3-6 minutes at 10-20 rpm; v) compressing the fourth mixture to obtain the pharmaceutical formulation; and vi) optionally film coating the pharmaceutical formulation with a Polyvinyl alcohol based coating system film.

In an embodiment of the present disclosure, the pharmaceutical composition is in the form of a tablet.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

EXAMPLES

The disclosure will now be illustrated with working examples, which is intended to illustrate the working of disclosure not intended to take restrictively to imply any limitations on the scope of the present disclosure. Unless defined otherwise, all technical and scientific terms used herein have the same meaning as commonly understood to any one of the ordinary skilled in the art to which this disclosure belongs. Although methods and materials similar or equivalent to those described herein can be used in the practice of disclosed methods and compositions, the exemplary methods, devices and materials are described herein. It is to be understood that this disclosure is not limited to particular methods, and experimental conditions described, as such methods and conditions may apply.

Example—1: Formulations

Four different formulations, namely formulation 1, 2, 3 and 4 were prepared by mixing all the constituents of the formulation in appropriate weight percentages, as provided below in Table 1-4.

TABLE 1

Formulation - 1

| Item # | Ingredients | Chlorpromazine Hydrochloride tablets 200 mg Amount per tablet (mg) | % w/w |
|---|---|---|---|
| 1 | Chlorpromazine Hydrochloride | 200.00 | 33.33 |
| 2 | Lactose Monohydrate | 208.00 | 34.67 |
| 3 | Microcrystalline cellulose | 120.00 | 20.00 |
| 4 | Pregelatinized Starch | 60.00 | 10.00 |
| 5 | Colloidal Silicon Dioxide | 3.00 | 0.50 |
| 6 | Magnesium Stearate | 9.00 | 1.50 |
| | Total weight of core tablet | 600.00 | 100.00 |
| | Coating | | |
| 7 | PVA Based coating system e.g. (Opadry II brown) | 24 | — |
| 8 | Purified water* | q.s | — |
| | Total weight of coated tablet | 624.00 | — |

TABLE 2

Formulation - 2

| Item # | Ingredients | Chlorpromazine Hydrochloride tablets 25 mg Amount per tablet (mg) | % w/w |
|---|---|---|---|
| 1 | Chlorpromazine Hydrochloride | 25.00 | 8.33 |
| 2 | Lactose Monohydrate | 144.20 | 48.07 |
| 3 | Microcrystalline cellulose | 83.20 | 27.73 |
| 4 | Pregelatinized Starch | 41.60 | 13.87 |
| 5 | Colloidal Silicon Dioxide | 1.50 | 0.50 |
| 6 | Magnesium Stearate | 4.50 | 1.50 |
| | Total weight of core tablet | 300.00 | 100.00 |
| | Coating | | |
| 7 | PVA Based coating system (Opadry II Brown) | 12.00 | — |
| 8 | Purified water* | q.s | — |
| | Total weight of coated tablet | 312.00 | — |

TABLE 3

Formulation - 3

| Item # | Ingredients | Chlorpromazine Hydrochloride tablets 25 mg Amount per tablet (mg) | % w/w |
|---|---|---|---|
| 1 | Chlorpromazine Hydrochloride | 25.00 | 5.56 |
| 2 | Lactose Monohydrate | 235.30 | 52.29 |
| 3 | Microcrystalline cellulose | 135.70 | 30.15 |
| 4 | Pregelatinized Starch | 45.00 | 10.00 |
| 5 | Colloidal Silicon Dioxide | 2.25 | 0.50 |
| 6 | Magnesium Stearate | 6.75 | 1.50 |
|  | Total weight of core tablet | 450.00 | 100.00 |
|  | Coating |  |  |
| 7 | PVA based coating system (Opadry II brown) | 18.00 | — |
| 8 | Purified water* | q.s | — |
|  | Total weight of coated tablet | 468.00 | — |

TABLE 4

Formulation - 4

| Item # | Ingredients | Chlorpromazine Hydrochloride tablets 100 mg Amount per tablet (mg) | % w/w |
|---|---|---|---|
| 1 | Chlorpromazine Hydrochloride | 100.00 | 33.33 |
| 2 | Lactose Monohydrate | 164.00 | 54.67 |
| 4 | Pregelatinized Starch | 30.00 | 10.00 |
| 5 | Colloidal Silicon Dioxide | 1.50 | 0.50 |
| 6 | Magnesium Stearate | 4.50 | 1.50 |
|  | Total weight of core tablet | 300.00 | 100.00 |
|  | Coating |  |  |
| 7 | PVA based coating system (Opadry II brown) | 12.00 | — |
| 8 | Purified water* | q.s | — |
|  | Total weight of coated tablet | 312.00 | — |

Example 2: Process of Preparing the Formulations 1-4

For this purpose, appropriate amounts of (i) chlorpromazine hydrochloride and microcrystalline cellulose; (ii) lactose monohydrate; and (iii) pre-gelatinized starch, colloidal silicon dioxide and magnesium stearate; as provided in table 1-4, were sieved through a #40 mesh screen attached with vibro sifter and collected in a polybag. Further, the sieved material was loaded into an octagonal blender for blending the ingredients of the composition. For this purpose, chlorpromazine hydrochloride and microcrystalline cellulose were blended for a period of 5 minutes at 15 rpm to obtain a first mixture. Similarly, lactose monohydrate was blended for a period of 10 minutes at 15 rpm to obtain a second mixture. Further, pre-gelatinized starch, colloidal silicon dioxide and magnesium stearate were blended for a period of 5 minutes at 15 rpm to obtain a third mixture. Further, the third mixture are sieved through a #40 mesh Further, dry blending the third mixture for a period of 5 minutes at 15 rpm to obtain a fourth mixture. The fourth mixture was further compressed to obtain a tablet dosage form of chlorpromazine hydrochloride. The obtained tablets are film coated with the target weight gain of 4% w/w using PVA based film coating system.

Advantages of the Present Disclosure

The present disclosure provides a process for preparation of process for preparation of the pharmaceutical formulation comprising: i) blending chlorpromazine hydrochloride and microcrystalline cellulose under a first set of pre-determined conditions to obtain a first mixture; ii) blending lactose monohydrate with first mixture under a second set of pre-determined conditions to obtain a second mixture; iii) blending pre-gelatinized starch, colloidal silicon dioxide and magnesium stearate with second mixture under a third set of pre-determined conditions to obtain a third mixture; iv) screening the third mixture through #40 Mesh and dry blending under a fourth set of pre-determined conditions to obtain a fourth mixture; and v) directly compressing the fourth mixture to obtain the pharmaceutical formulation. The pharmaceutical formulations of chlorpromazine hydrochloride prepared by the process of the present disclosure is simple, does not require the use of high energy, prolonged time periods or cost intensive processes, unlike the conventionally used processes.

We claim:
1. A pharmaceutical formulation consisting:
   a) chlorpromazine hydrochloride having a weight percentage in a range of 4-40% with respect to the pharmaceutical composition;
   b) magnesium stearate having a weight percentage in a range of 1-5% with respect to the pharmaceutical composition;
   c) lactose monohydrate having a weight percentage in a range of 30-55% with respect to the pharmaceutical composition;
   d) microcrystalline cellulose having a weight percentage in a range of 0-35% with respect to the pharmaceutical composition;
   e) pre-gelatinized starch having a weight percentage in a range of 3-15% with respect to the pharmaceutical composition; and
   f) colloidal silicon dioxide having a weight percentage in a range of 0.5-2.5%, with respect to the total mixture/ingredients in the pharmaceutical formulation.
2. The pharmaceutical formulation as claimed in claim 1, comprises about 10 mg to 200 mg of chlorpromazine hydrochloride.

* * * * *